United States Patent
Solazzi

(10) Patent No.: US 8,404,197 B2
(45) Date of Patent: Mar. 26, 2013

(54) SAMPLE CUP FOR USE IN SPECTROCHEMICAL ANALYSIS

(76) Inventor: Monte J. Solazzi, Palm City, FL (US)

( * ) Notice: Subject to any disclaimer, the term of this patent is extended or adjusted under 35 U.S.C. 154(b) by 812 days.

(21) Appl. No.: 11/880,997

(22) Filed: Jul. 25, 2007

(65) Prior Publication Data

US 2009/0028760 A1   Jan. 29, 2009

(51) Int. Cl.
*B01L 3/00* (2006.01)

(52) U.S. Cl. ........ 422/557; 422/400; 422/401; 422/500; 422/547; 422/550; 422/560; 422/561; 422/939; 422/940; 422/944; 600/573; 600/576; 600/580; 73/864.51; 73/864.53; 73/864.83; 73/864.84; 73/864.91; 206/438; 206/527; 220/269; 220/288; 220/319; 220/784; 220/793; 250/352; 250/428; 356/244; 356/246; 356/440; 378/45; 378/47; 378/18; 378/49; 378/83; 378/204; 378/208

(58) Field of Classification Search ........ 422/99, 422/102, 104, 939, 940, 400, 401, 500, 547, 422/549, 550, 557, 560, 561, 944; 600/573, 600/576, 580; 73/864.51, 864.53, 864.83, 73/864.84, 864.91; 206/438, 527; 220/269, 220/288, 319, 784, 793; 250/352, 428; 356/244, 356/246, 440; 378/45, 47, 48, 49, 79, 83, 378/204, 208

See application file for complete search history.

(56) References Cited

U.S. PATENT DOCUMENTS

| 4,346,299 A | * | 8/1982 | Mitteldorf et al. | ............ 378/204 |
| 4,575,869 A | * | 3/1986 | Torrisi et al. | ............ 378/47 |
| 5,323,441 A | * | 6/1994 | Torrisi et al. | ............ 378/44 |
| 5,630,989 A | | 5/1997 | Solazzi | |

* cited by examiner

*Primary Examiner* — Dennis M White
(74) *Attorney, Agent, or Firm* — Keene IP Law, LLC

(57) ABSTRACT

A cup assembly for holding a sample to be analyzed spectrochemically, includes a tubular longitudinal member which is disposed symmetrical about a central axis. The tubular member extends longitudinally between a first end and a second end. An indented peripheral flange is defined at the second end. The indented flange has an inverted L shaped cross-section. An annular collar extends longitudinally between a first end and a second end. An internal peripheral flange is defined at the first end. The internal flange has an inverted L shaped cross-section complementing the indented flange of the tubular member. When a substantially thin film is interposed between the second end of the tubular member and the first end of the annular collar, the film is retained between the sample cell body and the collar between the indented flange and the internal flange. The cup may have a funnel shaped sample retaining chamber.

22 Claims, 6 Drawing Sheets

FIG. 4A  FIG. 4B

SAMPLE CUP FOR USE IN SPECTROCHEMICAL ANALYSIS

FIELD OF THE INVENTION

This invention relates to a sample cup for use in holding specimens for spectrochemical analysis.

BACKGROUND OF THE INVENTION

The use and applications of thin-films to close substance containing sample cups are well recognized. An example of such a sample cup is disclosed in U.S. Pat. No. 5,630,989, entitled APPARATUS FOR TRIMLESS SAMPLE CUP USED IN X-RAY SPECTROSCOPY, the entire disclosure of which is hereby incorporated by reference herein.

Such sample cups are intended and designed to accommodate samples that are generally available in abundant quantities. However, when the sample quantity is small, it may be unevenly distributed on the thin film leading to imprecise results. Further, in some cases, samples have been found to leak at the interface of the thin film and the sample cups. Thus, there is a need for a sample cup which is better suited for a smaller sample quantity and which facilitates relatively uniform distribution of the sample over the thin film window. There is a need for a sample cup which reduces the likelihood of leakage of the sample at the interface of the thin film and the sample cup.

BRIEF DESCRIPTION OF THE DRAWINGS

Understanding of the present invention will be facilitated by considering the following detailed description of the preferred embodiments of the present invention taken in conjunction with the accompanying drawings, in which like numerals refer to like parts, and:

FIG. 2 illustrates the sample cup cell and the annular collar of FIG. 1 with a thin film interposed there between;

FIGS. 4A-4C illustrate a sample cup cell with integrated interior funnel shaped sample retaining chamber, according to an embodiment of the present invention;

DETAILED DESCRIPTION OF THE PREFERRED EMBODIMENTS

It is to be understood that the figures and descriptions have been simplified to illustrate elements that are relevant for a clear understanding of the present invention, while eliminating, for the purpose of clarity, many other elements found in typical sample cups and methods of making and using the same. Those of ordinary skill in the art may recognize that other elements and/or steps are desirable and/or required. However, because such elements and steps are well known in the art, and because they do not facilitate a better understanding of the present invention, a discussion of such elements and steps is not provided herein.

Figure 1A:
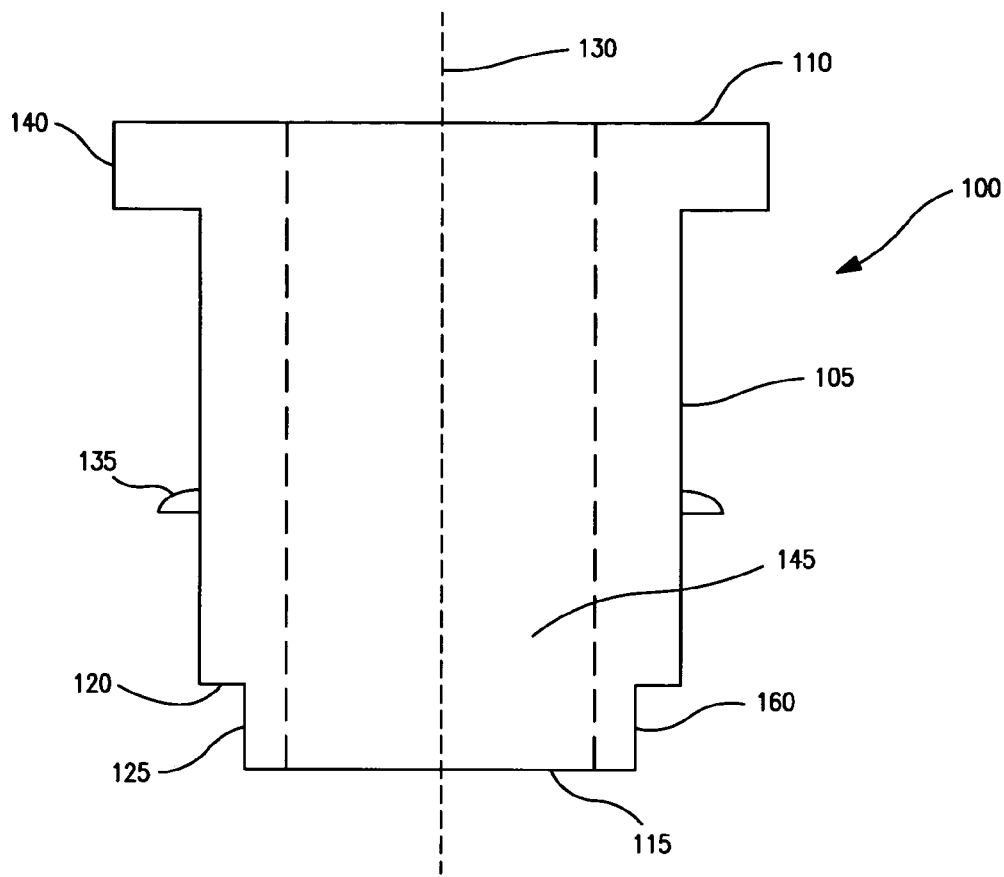
FIGS. 1A-1B illustrate a sample cup cell and an annular collar incorporating a flush fit between the cup and the collar according to an embodiment of the present invention.
Figure 1B:
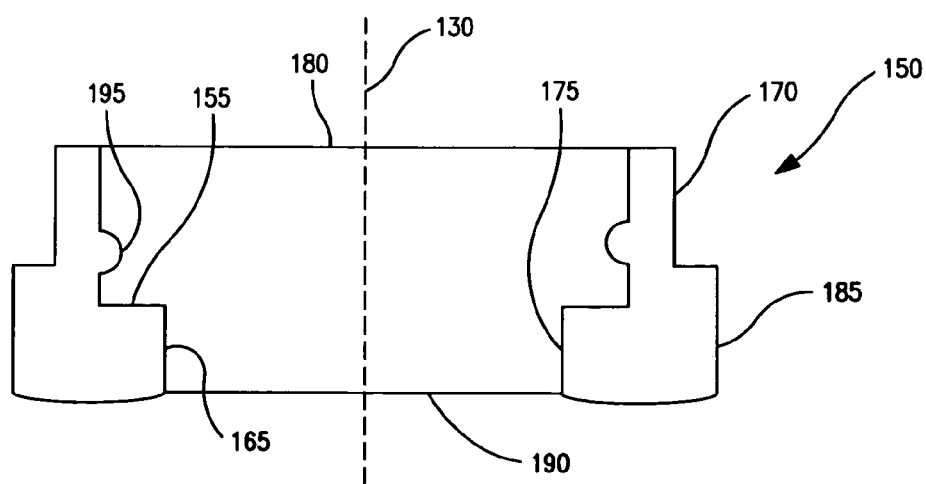

Referring now to FIG. 1A, there is shown a sample cup cell 100 and in FIG. 1B, an annular collar 150, according to an embodiment of the present invention. Sample cup cell 100 and annular collar 150 may each be formed of plastic, for example. In one particular embodiment, sample cups are between 0.894-0.897 inches in diameter, have an internal aperture of between 0.24-0.79 inches and are about 0.85 inch tall. Of course, other sizes are contemplated. Further, annular collar 150 may optionally be considerably shorter than sample cup cell 100.

Referring again to FIG. 1A, cell 100 includes a longitudinal tubular member 105 extending longitudinally between an open top end 110 of cell 100 and an open bottom end 115. Ends 110 and 115 have been designated as top and bottom respectively only for the ease of description. Tubular member 105 is symmetrically disposed about a central axis 130. A peripheral extending flange 140 is positioned around top end portion 110. Tubular member 105 and top and bottom ends 115, 110 define an open-ended inner cavity 145. At bottom open end 110, is an indented peripheral flange 160. Indented flange 160 has an inverted L shaped cross-section formed by surfaces 120 and 125. Surface 120 is transverse and substantially perpendicular to surface 125. In an exemplary embodiment of the invention, surfaces 120 and 125 form a right angle. A stop groove 135 is formed on exterior surface of tubular member 105 near bottom open end 115.

Referring now to FIG. 1B, annular collar 150 includes an annular member 170 extending longitudinally between a top open end 180 and a bottom end 190. Annular member 170 is also symmetrically disposed about central axis 130. A peripheral extending flange 185 is positioned around open end 190. Bottom open end 115 (FIG. 1A) of sample cup cell 100 is configured to receive annular collar 150. Top open end 180 of annular collar 150 is adapted to receive bottom open end 115 of cell body 105. Tubular member 170 has an internal protruding flange 175. Internal flange 175 has an inverted L shaped cross-section formed by two surfaces 155 and 165 defining a ledge. Surface 155 is transverse to and generally perpendicular to surface 165. In an exemplary embodiment of the invention, surfaces 155 and 160 form a right angle. Surfaces 155 and 165 complement cell body surfaces 120 (FIG. 1A) and 125 (FIG. 1A) respectively. Tubular member 170 has a projection ring 195 on its interior surface. Projection ring 195 is sized such that annular collar 150 fits snugly with the exterior surface of wall 105 of sample cup cell 100.

Figure 2:
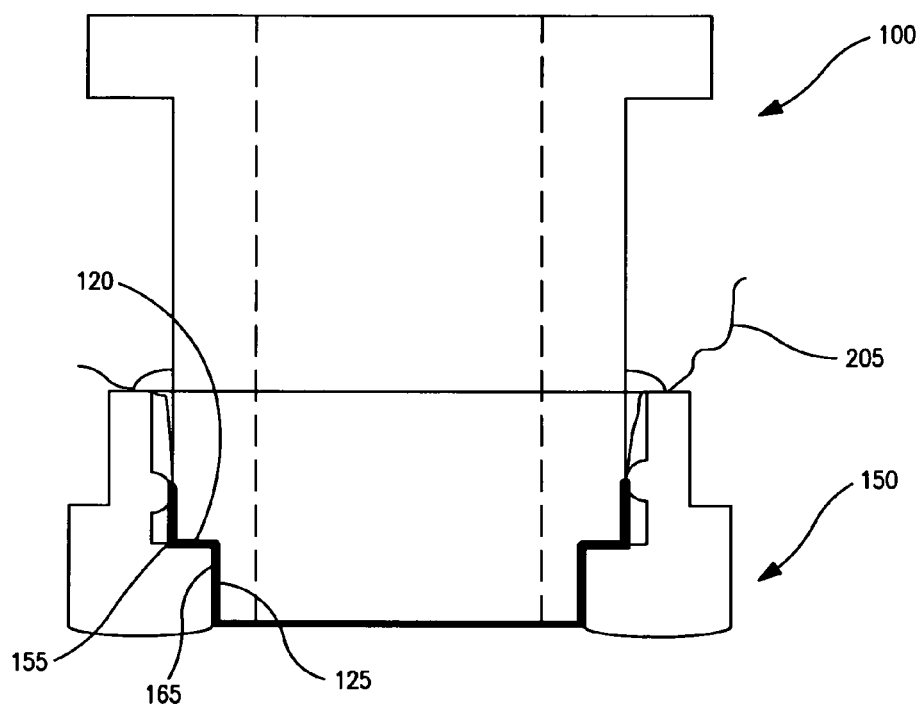

Referring to FIG. 2, in use a thin film 205 is interposed between cell 100 and annular collar 150. Thin film 205 is positioned over bottom open end 115 of cell 100. According to an embodiment of the present invention, thin film material 205 is flexible and transparent to radiant energy used in spectrochemical analysis. The possible compositions of such thin film materials 205 are well known in the art and need not be set forth herein at length. Annular collar 150 is positioned over film 205 and around cell 100. Annular collar 150 and cell 100 establish at least two seals between indented peripheral flange 160 of cell 100 and internal peripheral flange 175 of annular collar 150. One of the two seals is established between surfaces 125 and 165, while the other seal is established between surfaces 120 and 155. Thin film 205 is held taut between cell 100 and annular collar 150 at a right angle between surfaces 125 and 160. Thin film 205 is also held taut at another right angle between surfaces 120 and 155. Since the interface between annular collar 150 and cell 100 is generally at right angles, such a double seal may prevent any solution-type sample to leak through the interface. Thus, collar 150 may form taut, leak resistant thin-film windows for flat sample planes. Some liquid samples may tend to creep in between thin film and cell body wall in conventional sample cup cell assembly. The tight double seal formed between the cell body ledge, thin film and collar ledge would prevent such creeping in and avoid spillage of the liquid sample.

Figure 3:
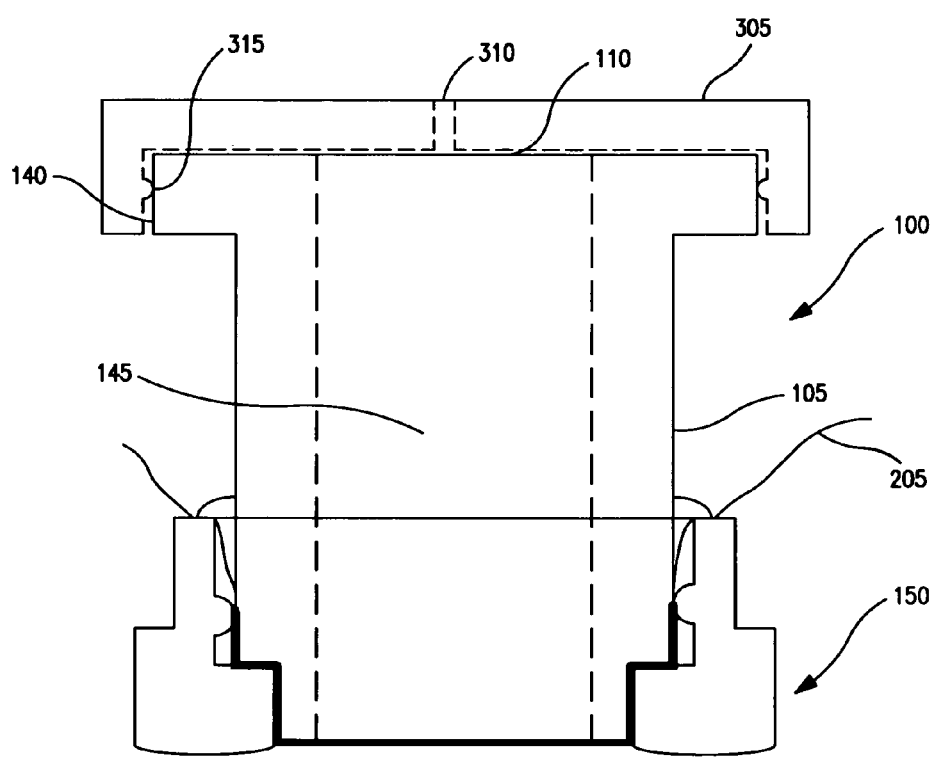
FIG. 3 illustrates the sample cup cell and the annular collar of FIG. 2 with a vented cap, according to an embodiment of the present invention.

Referring now to FIG. 3, a cap 305 is assembled over top open end 110 of sample cup 100. Cap 305 has a vent 310 to establish pressure differential equalization in air, vacuum or inert gas. Vented cap 305 may maintain pressure equalization to minimize potential convoluted sample plane formed by thin film 205 at bottom open end 115 (FIG. 1A). In an embodiment of the present invention, cap 305 has a projection ring 315 on its interior surface to establish a snug fit with peripheral flange 140 of cell 100. In another embodiment, cap 305 may be assembled over sample cup 100 via threads. The hollow space defined by body wall 105, thin film 205 and cap 305 forms a cavity or a sample retaining chamber 145.

Figure 4C:
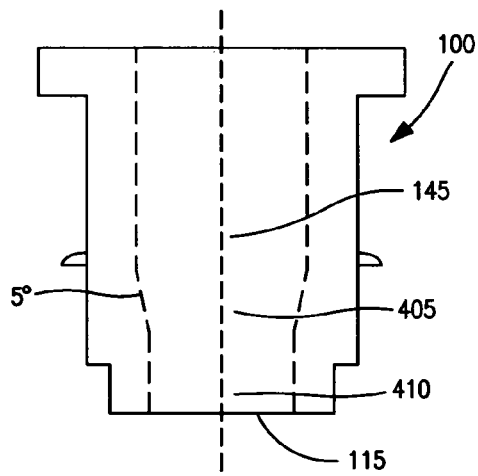
Figure 4C:
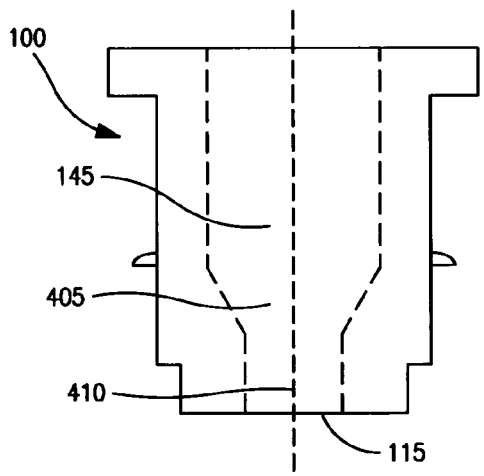
Figure 4C:
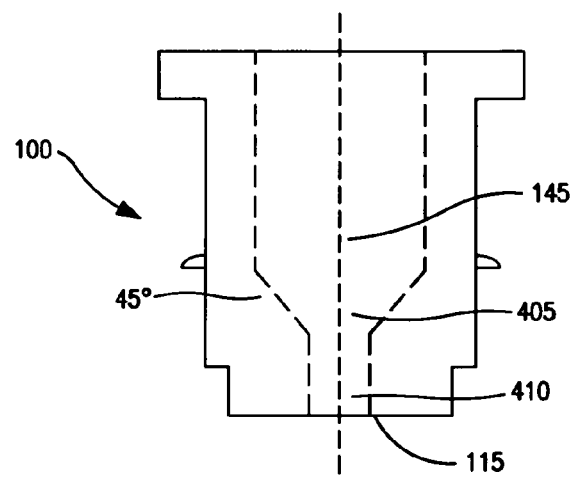

Referring to FIGS. 4A-4C, an embodiment of sample cup cell 100 is illustrated in each drawing. A funnel shaped chamber 145 is integrated within the cup cell 100. Funnel shaped chamber 145 has a larger conically shaped upper portion 405 and a lower spout 410. Larger conically shaped upper portion 405 allows and facilitates introduction of the sample substance and lower spout 410 of the funnel functions as the sample chamber. Larger conical shaped upper portion 405 may have different tapers ranging between 50 to 450. Spout 410 represents the aperture diameter of the sample cup 100. Bottom open end 115 of the cup, i.e. the aperture of spout 410 may be transformed into the sample plane formed by the attachment of a suitable thin film (205 of FIGS. 2, 3) with collar 150. In one particular embodiment, the aperture diameters are about 0.24 inch to 0.79 inch. Of course, other sizes are contemplated to be within the scope of the present invention. Such sample cups may handle a range of small or rare sample quantities with ease, analytical accuracy and precisions of measurements. Sample in such small quantities will be evenly distributed on the thin film because of relatively small size of aperture of spout 410. In one particular embodiment, sample cup cells 100 may accommodate micro sample quantity ranging from 0.11 cubic centimeters (cc) to 7.5 cc.

Figure 5A:
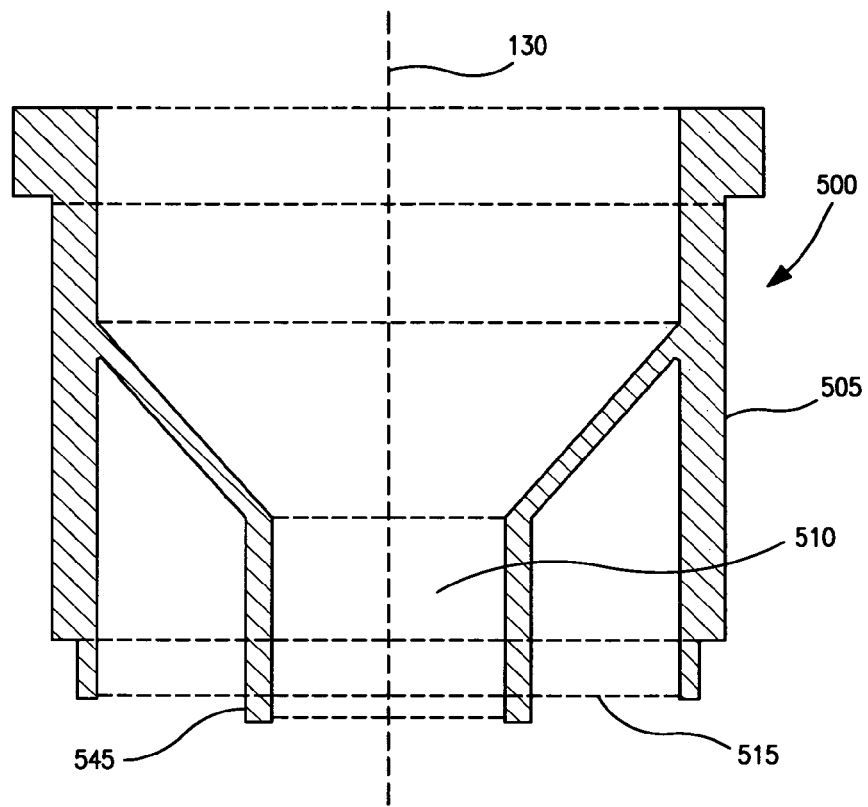
FIGS. 5A-5B illustrate cross sectional view of another embodiment of the sample cup cell with integrated interior funnel shaped sample retaining chamber, and a corresponding annular collar.
Figure 5B:
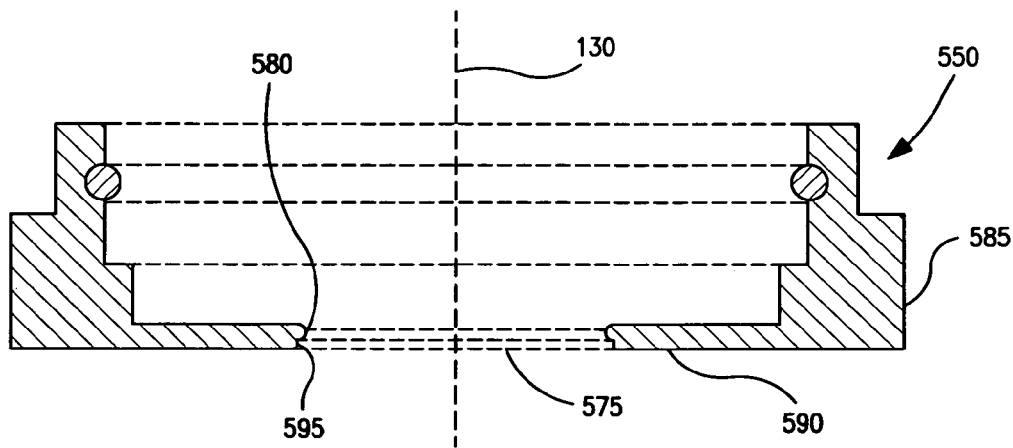

Referring now to FIG. 5A, an alternative embodiment of sample cup cell 500 is illustrated. Sample cup cell 500 has a tubular member 505 which is disposed symmetrically about a central axis 130. Tubular member 505 extends longitudinally about central axis 130. A lower spout 510 is defined by a wall 545. In an exemplary embodiment of the present invention, the sample cup cell 500 is hollow between tubular member 505 and wall 545. In an alternative embodiment, wall 545 may be integral with tubular member 505 and may be solid, for example as in FIGS. 4a-4c. Wall 545 extends a relatively small distance longitudinally, beyond tubular member 505 at lower open end 515. In an exemplary embodiment, lower spout 510 extends beyond tubular member 505 by a distance of about 0.085 inch. FIG. 5B illustrates an embodiment of annular collar 550 which is configured to be used with sample cell cup 500. Annular collar 550 has a bottom wall 590 with an aperture 575. Bottom wall 590 has a projecting bead 580 at least along a portion of the circumference of aperture 575. Bead 580 is formed on surface 595 of bottom wall 590. In an embodiment of the present invention, bead 580 is semispherical shaped. Aperture 575, along with bead 580, is sized to establish a snug fit with lower spout wall 545. Bottom wall 590 has thickness which is approximately the same as the distance by which wall 545 extends beyond tubular member 505. In an exemplary embodiment, bottom wall 545 has a thickness of about 0.085 inch.

Figure 6:
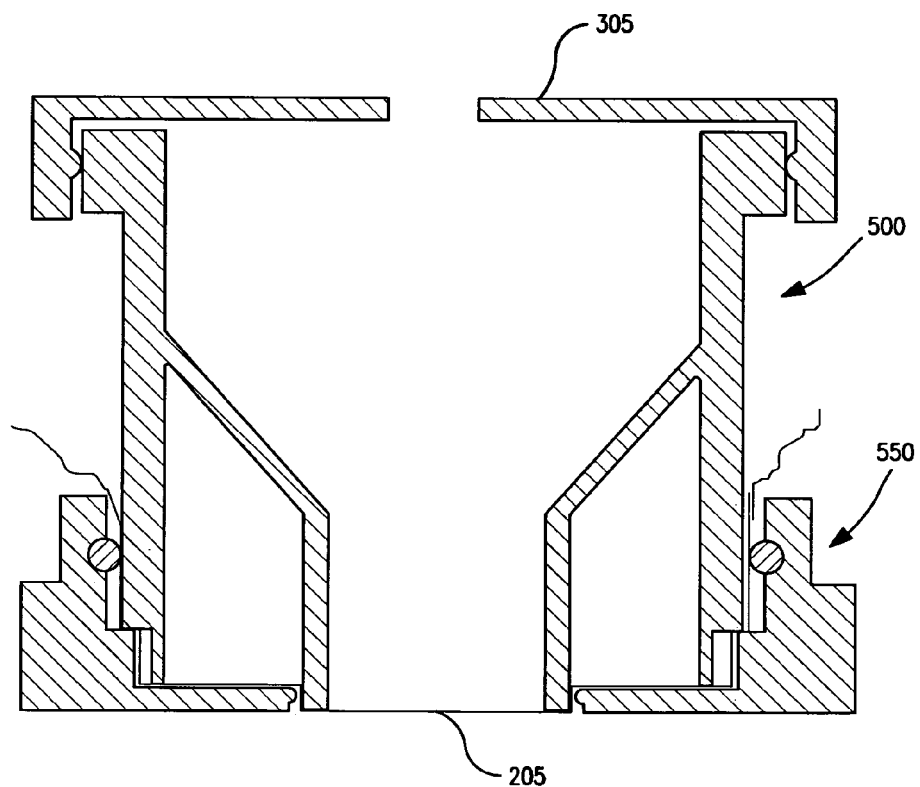
FIG. 6 illustrates cross-sectional view of the annular collar of FIG. 5B holding a thin film over sample cup cell of FIG. 5A, according to an alternative embodiment of the present invention.

FIG. 6 illustrates a thin film 205 interposed between sample cup cell 500 and annular collar 550. A vented snap-on cap 305 seals sample cup cell 500. Thin film 205 is mechanically clamped to lower spout 510 by bottom wall 590 of annular collar 550. Such mechanical clamping prevents a liquid sample from spreading on the thin film 205 beyond aperture of spout 510 and ensures that liquid sample is confined within spout 510. When sample cup cell 500 and annular collar 550 are assembled along with thin film 205, bottom wall 590 and thin film 205 are substantially planar to each other.

Those of ordinary skill in the art may recognize that many modifications and variations of the present invention may be implemented without departing from the spirit or scope of the invention. Thus, it is intended that the present invention covers the modifications and variations of this invention.

What is claimed is:

1. A cup assembly for holding a sample to be analyzed spectrochemically, comprising:
   a tubular longitudinal member disposed symmetrically about a central axis, said tubular member extending longitudinally between a first end and a second end thereof, said tubular member defining an open-ended cylindrical inner cavity extending longitudinally between said first end and said second end, said tubular member including an indented peripheral flange defined at said second end, said indented peripheral flange having an inverted L shaped cross-section, the outer surface of said indented peripheral flange forming a series of substantially right angles; and
   an annular collar extending longitudinally between a first end and a second end thereof, with an internal peripheral flange defined at said first end of said annular collar, and an internal projection ring defined adjacent said internal peripheral flange, said internal peripheral flange having an inverted L shaped cross-section complementing said outer surface of said indented peripheral flange of said tubular member;
   wherein, upon assembly, a substantially thin film is interposed between said second end of said tubular member and said first end of said annular collar, said second end of said tubular member is inserted into said first end of said annular collar, and said film is retained between the tubular member and the collar in a series of three substantially right angles adjacent an interface between said indented peripheral flange and said internal peripheral flange, and an outer surface of said tubular member and said internal projection ring.

2. The cup assembly according to claim 1, wherein said substantially thin film is transparent to radiant energy utilized in spectrochemical analysis.

3. The cup assembly according to claim 1, wherein said first end of said tubular member is an open end.

4. The cup assembly according to claim 1, further comprising a cap, said cap configured to cover said first end of said tubular member.

5. The cup assembly according to claim 4, wherein said cap is a snap-on cap.

6. The cup assembly according to claim 4, wherein said cap further comprises threads.

7. The cup assembly according to claim 4, wherein said cap has a vent aperture.

8. The cup assembly according to claim 4, wherein said cap has a projection ring on its interior.

9. The cup assembly according to claim 1, wherein said annular collar has a length substantially smaller than the length of said tubular member.

10. The cup assembly according to claim 1, wherein said tubular member further comprises an outwardly extending annular flange unitarily formed with said first end of said tubular member.

11. The cup assembly according to claim 1, further comprising a stop groove.

12. A cup assembly for holding a sample to be analyzed spectrochemically, comprising:

a tubular member symmetrically disposed about a central axis, said tubular member extending longitudinally between a first open end and a second open end, said member defining an interior funnel shaped chamber extending from said first open end to said second open end, said chamber including an upper conical section defined adjacent said first open end with a portion of said conical section continually tapering toward said central axis at a selected angle to a relatively narrow lower cylindrical spout section defined adjacent said second open end; and an annular collar extending longitudinally between a first end and a second end thereof, wherein, upon assembly, a substantially thin film is interposed between said second open end of said tubular member and said first end of said annular collar, said second open end of said tubular member is inserted into said first end of said annular collar, and said film is retained between the tubular member and the collar.

13. The cup assembly of claim 12, further comprising:

an indented peripheral flange, said indented flange defined at said second end of said tubular member, said indented flange having an inverted L shaped cross-section; and an internal peripheral flange defined at said first end of said annular collar, said internal flange having an inverted L shaped cross-section complementing said indented flange of said tubular member, wherein when a substantially thin film is interposed between said second end of said tubular member and said first end of said annular collar, and said second end of said tubular member is inserted into said first end of said annular collar, said film is retained between the tubular member and the collar between said indented flange and said internal flange.

14. The cup assembly according to claim 12, wherein said substantially thin film is transparent to radiant energy utilized in spectrochemical analysis.

15. The cup assembly according to claim 12, further comprising a cap, said cap configured to cover said first end of said tubular member.

16. The cup assembly according to claim 12, wherein said cap is a snap-on cap.

17. The cup assembly according to claim 12, wherein said cap has a vent aperture.

18. The cup assembly according to claim 12, wherein said cap has a projection ring on its interior.

19. The cup assembly according to claim 12, wherein said tubular member further comprises an outwardly extending annular flange unitarily formed with said first end of said tubular member.

20. The cup assembly according to claim 12, wherein said annular collar has a projection on its interior surface.

21. The cup assembly according to claim 12, wherein said relatively narrow spout section extends beyond said tubular member; and wherein said annular collar further comprises a bottom wall having an aperture, said aperture being slightly larger than said spout section.

22. The cup assembly according to claim 21, wherein said bottom wall further comprises a projecting bead along at least a portion of the circumference of said aperture.

* * * * *